United States Patent [19]

Cheng et al.

[11] 4,342,877
[45] Aug. 3, 1982

[54] PROCESS FOR THE PREPARATION OF α-HALOGENATED CRESOL ESTERS

[75] Inventors: Dah-Chieh O. Cheng; Joseph S. Bowers, Jr.; Ronald J. Maner, all of Kingsport, Tenn.

[73] Assignee: Eastman Kodak Company, Rochester, N.Y.

[21] Appl. No.: 93,661

[22] Filed: Nov. 13, 1979

[51] Int. Cl.³ .................. C07C 67/287; C07C 69/24; C07C 69/157
[52] U.S. Cl. .................. 560/130; 260/465 F; 260/544 Y; 560/144; 562/606; 562/607; 564/124
[58] Field of Search ........................................ 560/130

[56] References Cited

U.S. PATENT DOCUMENTS 3,226,446 12/1965 Drain et al. .................. 560/130

Primary Examiner—Vivian Garner

Attorney, Agent, or Firm—J. Frederick Thomsen; Daniel B. Reece, III

[57] ABSTRACT

Process for the preparation of Compound I by treating Compound II with $X_2$ or $SO_2X_2$ in the presence of a free radical initiator and an anhydride having the formula $(RCO)_2O$ while eliminating the acid halide formed having the formula RCOX from the reaction mixture, wherein Compounds I and II have the formulas

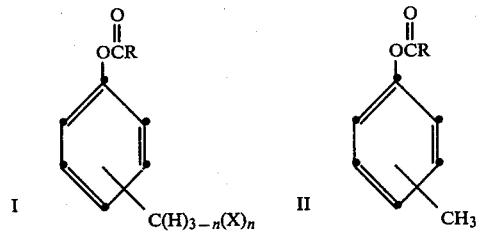

and R is $C_1$–$C_3$ alkyl, X is Cl or Br and n is 1, 2 or 3.

9 Claims, No Drawings

PROCESS FOR THE PREPARATION OF α-HALOGENATED CRESOL ESTERS

The invention relates to a novel halogenation process and, more particularly, to the halogenation, i.e., chlorination or bromination, of the methyl group of cresol carboxylic acid esters.

The preparation of α-halocresol carboxylic acid esters by the halogenation of cresol carboxylic acid esters requires the use of moderate temperatures if displacement of the acyloxy group is to be avoided. Since little, if any, halogenation occurs at such temperatures, the reaction requires the use of a free radical initiator such as a peroxide, e.g., dibenzoyl peroxide or di-t-butyl peroxide, or an azo compound, e.g., azobisisobutyronitrile. The preparation of 4-acetoxybenzyl bromide by treating p-cresol acetate with N-bromosuccinimide in the presence of dibenzoyl peroxide is disclosed at J. Chem. Soc. 1953, 773. The commercial use of N-halosuccinimide and analogous compounds (C.A. 53:264b) as halogenating agents is not desirable because of their high cost.

Initial attempts to halogenate cresol carboxylic acid esters using chlorine, bromine, sulfuryl chloride or sulfuryl bromide and a free radical initiator in an inert solvent were not successful. The use of such halogenating agents causes the formation of free hydrohalogen acid which converts the ester reactant to free cresol which in turn inactivates the free radical initiator. The use of conventional acid scavengers such as sodium acetate and sodium carbonate did not prevent the formation of free cresol.

We have discovered that good yields of α-halocresol carboxylic acid esters can be prepared by treating the corresponding cresol carboxylic acid ester with chlorine, bromine, sulfuryl chloride or sulfuryl bromide in the presence of a free radical initiator and a carboxylic acid anhydride while eliminating the carboxylic acid halide formed from the reaction mixture. The hydrohalogen acid generated during the halogenation process reacts with the anhydride to produce an acid and an acid halide. By eliminating the latter from the reaction mixture, formation of free cresol is avoided.

In its broader aspects, our novel process comprises the preparation of Compound I by treating Compound II with $X_2$ or $SO_2X_2$ in the presence of a free radical initiator and an anhydride having the formula $(RCO)_2O$ while eliminating the acid halide formed having the formula RCOX from the reaction mixture, wherein Compounds I and II have the formulas

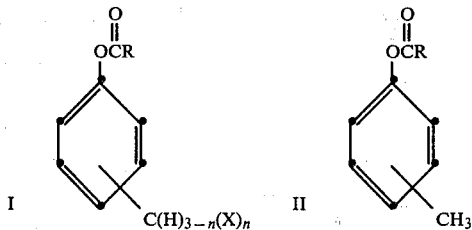

and R is $C_1$–$C_3$ alkyl, X is Cl or Br and n is 1, 2 or 3. Although our work has been concerned primarily with the synthesis of p-acyloxybenzyl halides, our improved process can be utilized to prepare the α,α-di- and α,α,α-tri-halocresol esters encompassed by formula I.

The amount of halogenating agent ($X_2$ or $SO_2X_2$) that is used will depend on the desired product, i.e., on whether n is 1, 2 or 3. When n is 1, the mole ratio of cresol ester to mole of halogenating agent can be up to about 1.0 although the use of ratios approaching 1.0 results in the formation of significant amounts of dihalogenated product, i.e., wherein n is 2. Thus, in preparing compounds in which n is 1, it is advantageous to use ratios of about 0.6 to 0.75 and to recover starting material during the product work-up, e.g., by distillation. Since the dihalo compound is useful in the synthesis of p-hydroxybenzaldehyde, a pharmaceutical and dye intermediate, its co-production in the process is not necessarily undesirable. When the desired product is the dichlorocresol ester, the mole ratio should be in the range of about 1.5 to 2 whereas preparation of the trichloro compound will require the use of ratios of 3 or more.

The amount of anhydride that may be used will be at least one mole per mole of halogenating agent. The use of excess anhydride is not detrimental to the practice of the process and thus the upper limit of the anhydride:-halogenating agent mole ratio is not important. However, the use of ratios greater than about 1.5 are not practical since the excess anhydride usually will be decomposed during product isolation such as is described in the examples herein. The amount of halogenation-promoting, free radical initiator which will effectively promote the halogenation reaction will be in the range of about 0.01 to 0.05 moles initiator per mole of cresol ester reactant depending on the particular product that is desired.

The halogenation process can be carried out at temperatures of about 60° to 85° C., preferably at about 70° to 80° C. Atmospheric or sub-atmospheric pressures may be used. Since the use of an anhydride is an important feature of our process, it should be carried out under essentially anhydrous conditions. Additional inert solvents such as carbon tetrachloride and chlorobenzene also can be employed.

As indicated above, hydrochloric or hydrobromic acid formed during the process reacts with the anhydride to form an acid and an acid halide. The acid halide must be eliminated from the reaction mixture to avoid formation of unesterified cresol. The acid halide may be chemically eliminated by carrying out the process in the presence of an acid scavenging agent which decomposes the acid halide. Examples of such acid scavenging or acid binding agents include the alkali metal salts of $C_2$–$C_4$ carboxylic acids and the alkali metal carbonates. When this technique of eliminating the acid halide is used, at least one equivalent of acid scavenger should be used per mole of halogenation agent used, e.g., at least one mole of sodium acetate or one-half mole sodium carbonate. In certain cases it may be convenient to use a large excess of a carboxylic acid alkali salt as is shown in Example 1.

The second technique for eliminating the acid halide is by carrying out the process under a reduced pressure which permits the acid halide, and carboxylic acid, to be distilled from the reaction mixture. The upper limit of the reduced pressure required will depend upon the temperature employed. Pressures in the range of about 100 to 200 mm. Hg. usually will give satisfactory results.

A preferred embodiment of our novel process comprises the preparation of p-acetoxybenzyl chloride by treating p-tolyl acetate with about 0.6 to 1.0 mole of $Cl_2$ per mole of p-tolyl acetate at a temperature of about 60° to 85° C. in the presence of a free radical initiator and acetic anhydride while eliminating the acetyl chloride formed from the reaction mixture.

The compounds obtained from the process described hereinabove are useful chemical intermediates. For example, p-acetoxybenzyl chloride can be converted to p-acetoxybenzyl acetate which in turn can be reacted with an alkali cyanide (Bull. Inst. Chem. Res., Kyoto Univ., Vol. 52, No. 3, 514) to yield p-hydroxyphenylacetonitrile. Partial hydrolysis of the nitrile gives p-hydroxyphenylacetamide, a compound useful in the synthesis of the pharmaceutical Atenolol.

Our process is further illustrated by the following examples.

EXAMPLE 1

A mixture of p-cresol (108 g., 1.0 mole) and acetic anhydride (16.6 ml., 18.0 g., 0.18 mole) was heated at 130° C. while acetic anhydride (87 ml., 94 g., 0.92 mole) was added over a 30 minute period (a gentle exotherm slowly brought the mixture to reflux). This solution was further heated at reflux (150° C.) for one hour and then acetic acid was distilled off until the pot temperature reached 195° C. Heating of the mixture containing p-cresol acetate was discontinued and acetic anhydride (99 ml., 1.0 mole) was added. The mixture was cooled to 50° C. and anhydrous sodium acetate (131 g., 1.6 mole) was added followed by 3.0 g. of azobisisobutyronitrile (AIBN). After heating to 70° C. chlorine (49 g., 0.69 mole) was added through a gas dispersion tube below the surface of the liquid over a period of 1–2 hours while maintaining the temperature between 70°–75° C. The reaction was mildly exothermic and required some cooling. Upon completion of the chlorine addition, the p-acetoxybenzyl chloride thus obtained was converted to p-acetoxybenzyl acetate by refluxing (150° C.) the reaction mixture for 4 hours. The reaction mixture is cooled to 60°–65° C. and 10 ml. water is added to destroy remaining acetic anhydride. The temperature is controlled at 70°–75° C. while four 10 ml. portions of water are added at 30-minute intervals. The mixture is then cooled to 35° C. and drowned into 300 ml. water. After all salts are dissolved the layers are allowed to separate and the aqueous layer is discarded. Toluene (200 ml.) is added to the organic phase and the resulting solution is washed three times with water. The toluene solution then was distilled to give the following fraction.

(a) 168 g. water-wet toluene collected up to 140° C. at 100–150 mm. Hg.
(b) 60 g. (0.4 mole) of p-tolyl acetate collected between 80°–130° C. at 5 mm. Hg.
(c) 105 g. (0.5 mole) of p-acetoxybenzyl acetate collected between 130°–160° C. at 5 mm. Hg.

This represents an 85% yield of p-acetoxybenzyl acetate based on the p-tolyl acetate consumed.

EXAMPLE 2

To a mixture containing p-cresyl acetate (prepared by the acetylation of 324 g. p-cresol according to the procedure of Example 1) was added acetic anhydride (312 ml., 337.6 g., 3.3 mole). After cooling the mixture to 75° C., 9 g. of AIBN was added. A vacuum of 185–190 mm. Hg was applied and then chlorine (213 g., 3.0 mole) was added over a period of 2.5 hours while maintaining a temperature below 80° C. During the chlorine addition, 295 ml. of distillate, a mixture of acetyl chloride and acetic acid, was collected. The vacuum was replaced by a nitrogen atmosphere and 246 g. (3 mole) of sodium acetate was added at 75° C. over a period of 30 minutes. Acetic acid (200 ml.) also was added to the reaction mixture which then was refluxed (150° C.) for two hours. Following 2 hours of additional stirring, the mixture was drowned into 500 ml. of cold water. The top organic layer was separated and distilled under reduced pressure (4 Torr.) and the following fractions were recovered:

(a) 40°–95° C. —150.7 g. p-cresyl acetate containing a trace amount of acetic anhydride; and
(b) 95°–165° C. —400 g. p-acetoxybenzyl acetate.

This represents a 96% yield of p-acetoxybenzyl acetate, based on the p-cresyl acetate consumed and a yield of above 96% of p-acetoxybenzyl chloride. Similar results were obtained when a mixture containing 2 moles of p-cresyl acetate was treated with bromine (112.8 ml., 351.8 g., 2.2 mole) under a vacuum of 100–110 mm. Hg.

EXAMPLE 3

To a mixture of 225 g. (1.5 mole) of p-tolyl acetate, 168.3 g. of acetic anhydride and 4.5 g. AIBN at 75° C. and under a vacuum of 185–190 mm. Hg. was added 223 g. (134 ml., 1.65 mole) of sulfuryl chloride over a period of 30 minutes. A distillate immediately was condensed in both dry ice and wet ice traps. The reaction mixture was then stirred at 75° C. for an additional 10 minutes. Sodium acetate (123 g., 1.5 mole) was added over a 15-minute period and the mixture was heated at 135° C. for 1.5 hours. Acetic acid (110 ml.) was added and the reaction mixture was refluxed for an additional hour. Following the addition of 275 ml. of water at room temperature, the organic layer was collected and distilled at 3–4 torr. to give the following fractions.

(a) 48.6 g. tolyl acetate at 75°–100° C.
(b) 220 g. of p-acetoxybenzyl chloride at 100°–155° C.

The invention has been described in detail with particular reference to certain preferred embodiments thereof, but it will be understood that variations and modifications can be effected within the spirit and scope of the invention.

We claim:

1. Process for the preparation of Compound I by treating Compound II with $X_2$ or $SO_2X_2$ at a temperature of about 60° to 85° C. in the presence of a halogenation-promoting free radical initiator and an anhydride having the formula $(RCO)_2O$ while eliminating the acid halide formed having the formula RCOX from the reaction mixture, wherein Compounds I and II have the formulas

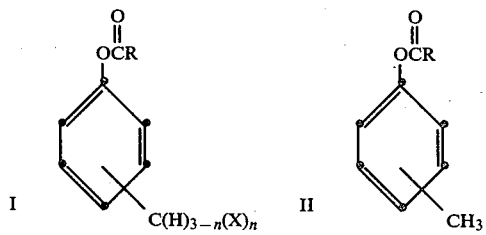

and R is $C_1$–$C_3$ alkyl, X is Cl or Br and n is 1, 2 or 3.

2. Process according to claim 1 wherein the acid halide is eliminated by carrying out the process in the presence of an alkali metal salt of a $C_2$–$C_4$ carboxylic acid or an alkali metal carbonate.

3. Process according to claim 1 wherein the acid halide is eliminated by carrying out the process under reduced pressure while distilling the acid halide from the reaction mixture.

4. Process for the preparation of Compound I which comprises treating Compound II with about 0.6 to 1.0 mole of $X_2$ or $SO_2X_2$ per mole of Compound II at a temperature of about 60° to 85° C. in the presence of a halogenation-promoting free radical initiator and acetic anhydride while eliminating the acetyl halide formed from the reaction mixture, wherein Compounds I and II have the formulas

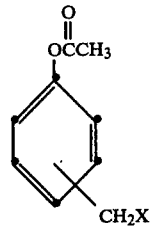
I

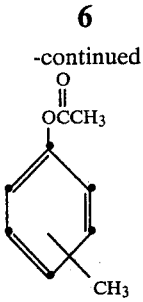
II and X is Cl or Br.

5. Process according to claim 4 wherein the acid halide is eliminated by carrying out the process in the presence of at least one equivalent of an alkali metal salt of a $C_2$–$C_4$ carboxylic acid or an alkali metal carbonate and the free radical initiator is azobisisobutyronitrile, dibenzoyl peroxide or di-t-butyl peroxide.

6. Process according to claim 5 wherein X is Cl, Compound I is p-acetoxybenzyl chloride and Compound II is p-tolyl acetate.

7. Process according to claim 4 wherein the acid halide is eliminated by carrying out the process under reduced pressure while distilling the acid halide from the reaction mixture and wherein the free radical initiator is azobisisobutyronitrile, dibenzoyl peroxide or di-t-butyl peroxide.

8. Process according to claim 7 wherein X is Cl, Compound I is p-acetoxybenzyl chloride and Compound II is p-tolyl acetate.

9. Process for the preparation of p-acetoxybenzyl chloride which comprises treating p-tolyl acetate with about 0.6 to 1.0 mole of chlorine per mole of p-tolyl acetate at a temperature of about 60° to 85° C. in the presence of (1) an effective amount of a halogenation-promoting free radical initiator, (2) at least one mole of acetic anhydride per mole of chlorine and (3) at least one mole of sodium acetate per mole of chlorine.

* * * * *